(12) United States Patent
Ries

(10) Patent No.: US 7,182,089 B2
(45) Date of Patent: Feb. 27, 2007

(54) MAGNETICALLY NAVIGABLE DEVICE WITH ASSOCIATED MAGNETIC ELEMENT

(75) Inventor: Günter Ries, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 218 days.

(21) Appl. No.: 10/943,912

(22) Filed: Sep. 20, 2004

(65) Prior Publication Data

US 2005/0062562 A1 Mar. 24, 2005

(30) Foreign Application Priority Data

Sep. 19, 2003 (DE) ................................ 103 43 494

(51) Int. Cl.
*A61B 19/00* (2006.01)
*A61B 5/05* (2006.01)
(52) U.S. Cl. ...................................... 128/899; 600/114
(58) Field of Classification Search ................. 128/899; 600/114, 117
See application file for complete search history.

(56) References Cited

U.S. PATENT DOCUMENTS

| | | | | |
|---|---|---|---|---|
| 3,188,639 | A | * | 6/1965 | Cook et al. ................. 342/353 |
| 3,745,386 | A | * | 7/1973 | Lloyd .......................... 310/13 |
| 5,125,888 | A | | 6/1992 | Howard et al. |
| 5,353,807 | A | | 10/1994 | DeMarco |
| 5,681,260 | A | | 10/1997 | Ueda et al. |
| 6,230,038 | B1 | | 5/2001 | Von Gutfeld et al. |
| 6,776,165 | B2 | * | 8/2004 | Jin ............................. 128/899 |
| 2003/0139661 | A1 | | 7/2003 | Kimchy et al. |

FOREIGN PATENT DOCUMENTS

| DE | 101 42 253 | 4/2003 |
|---|---|---|
| WO | 96/03795 | 2/1996 |
| WO | 03/028224 | 4/2003 |

OTHER PUBLICATIONS

Mosse et al, "Electrical Stimulation for Propelling Endoscopes", Gastrointestinal Endoscopy, vol. 54, No. 1, 2001, pp. 79-83.
Meeker et al., "Optimal Realization of Arbitrary Forces in a Magnetic Stereotaxis System", IEEE Transactions on Magnetics, vol. 32, No. 2, Mar. 1996, pp. 320-328.

* cited by examiner

*Primary Examiner*—Ramon M. Barrera
(74) *Attorney, Agent, or Firm*—Staas & Halsey LLP

(57) ABSTRACT

A magnetically navigable device has a magnet element with a greater extent in one direction than at right angles thereto. The magnet element is arranged asymmetrically with respect to a central axis of the device which points in the direction in which the magnet element extends. The device may be, for example, a video capsule from medical technology, such as for endoscopy.

29 Claims, 3 Drawing Sheets

MAGNETICALLY NAVIGABLE DEVICE WITH ASSOCIATED MAGNETIC ELEMENT

CROSS REFERENCE TO RELATED APPLICATIONS

This application is based on and hereby claims priority to German Application No. 103 43 494.1 filed on 19 Sep. 2003, the contents of which are hereby incorporated by reference.

BACKGROUND OF THE INVENTION

1. Field of the Invention

The invention relates to a magnetically navigable device with at least one associated magnet element which has a greater extent in one direction than at right angles thereto. The device can be assigned a central axis which points in this direction in which the magnet element extends. Such a magnetically navigable device can be found in DE 101 42 253 C1.

2. Description of the Related Art

In medicine, use is made of probe-like devices such as endoscopes or catheters which are inserted into a proband through incisions or body orifices and can be displaced externally in the longitudinal direction and hence can be navigated in one dimension. Optical fibers permit visual inspection, with control wires being able to be used to swivel an endoscope tip and hence the viewing direction. It is thus possible to produce devices for biopsies, in particular. However, the probe-like devices used in this context have only limited navigability, particularly at branch points, which means that contactless exertion of force from outside might entail an expansion of the field of application. Such an exertion of force can be brought about magnetically.

The publication "IEEE Transactions on Magnetics", Vol. 32, No. 2, March 1966, pages 320 to 328 and U.S. Pat. No. 5,125,888 A discloses a magnet coil system for such contactless magnetic probe control. The coils in the system can be used to generate variable field directions and field gradients, in order to guide or move a magnetic probe device, such as a catheter with magnetic material or magnetic implants, in a body to be examined, for example a human body, for the purposes of therapy.

WO 96/03795 A1 describes a method with additional pulse coils which can be used for moving a magnetic probe device in steps by precisely defined current pulses under computer control.

"Video capsules" used for inspecting the digestive tract are also known, by way of example, from the journal "Gastrointestinal Endoscopy", Vol. 54, No. 1, 2001, pages 79 to 83. In this context, however, the video capsule is moved by the natural intestinal movement; that is to say that the movement and the viewing direction of the capsule are purely random.

DE 101 42 253 C1 cited at the outset discloses a corresponding, largely cylindrical video capsule which thus has a pronounced extent in the direction of a longitudinal axis. This capsule is equipped with a bar magnet and also with video apparatuses and other intervention apparatuses. Forces for navigation are intended to be exerted on the bar magnet by an external magnet coil system (not described in more detail). Mention is made of a freely suspended "helicopter mode" with external control by a 6D mouse, feedback of the force via the mouse and positional feedback by a transponder. The known video capsule's bar magnet extends centrally along the axis, which means that the common center of gravity of the video capsule and of the bar magnet is situated on this axis. It is thus not possible to control the degree of rotational freedom about the longitudinal axis magnetically, however. The consequence of this is that a prescribed position, for example the "top" position, on a transmitted video image does not match the corresponding "top" position in a co-ordinate system in the video capsule.

SUMMARY OF THE INVENTION

It is an object of the present invention to configure the magnetically navigable device with the features mentioned at the outset such that the rotary position about the longitudinal axis of the device is clearly identifiable.

Accordingly, the magnetically navigable device having at least one associated magnet element, which has a greater extent in one direction than at right angles thereto, and having a central axis pointing in this direction of extent is intended to be configured such that the magnet element is arranged asymmetrically with respect to the axis of the device.

With the inventive arrangement of the magnet element relative to the navigable device, it is assumed that in a local magnetic field the at least one magnet element with its pronounced extent and hence the entire device are oriented in the direction of the field lines of the local magnetic field. In line with the invention, the magnet element is intended to be mounted asymmetrically with respect to an axis which runs through the center of the device (without the magnet element) and points in the direction in which the magnet element extends. In general, this axis is the longitudinal axis of the device, although the shape of the device is inherently arbitrary. The consequence of the asymmetric arrangement of the magnet element with respect to this axis is that the magnetic force generated by magnetic field gradients also engages approximately at the center of gravity of the magnet element and hence produces no vertical levitation. In this case, the gravitational force engages at the mass center, which is moved more toward the longitudinal axis of the device. As the pair of forces formed by gravitational force and compensating magnetic force interact, a freely suspended device then rotates such that the magnet element or the combination of all magnet elements or element parts adopts the "top" position, i.e. counter to the gravitational force. The device is thus permanently associated with "the top", independently of position and orientation. Advantageously, navigation of the device by sight using a video screen is thus simplified, e.g. when the device contains a video camera, since the "top" orientation of the transmitted video image coincides with the "top" direction on the video screen. A corresponding magnetically navigable device can be used particularly in the field of medical technology, particularly endoscopy.

The device may advantageously contain a support structure whose outside has the magnet element arranged on it. A corresponding design can be produced easily. This is because the device itself, such as a video capsule, usually represents such a support structure.

Preferably, the support structure has a shape which is at least largely rotationally symmetrical with respect to the longitudinal axis, particularly at least largely cylindrical.

The magnet element may advantageously be in the form of a half-shell-shaped or saddle-shaped or bar-shaped element. It can be prefabricated and mounted externally on or integrated into the device.

Advantageously, the transverse extent of the magnet element may be chosen to be no more than equal to half the longitudinal extent thereof. Corresponding extent conditions simplify secure movement of the device provided with the element in a magnetic field. Preferably, a magnet element is chosen whose mass is between 0.2 times and 4 times that of the device without the magnet element. Corresponding weight conditions simplify the navigability of the device in the magnetic field.

Advantageously, the device is provided with shorted conductor loops made of material having good electrical conductivity. Such conductor loops can be used to achieve eddy current damping for oscillations in the direction of the longitudinal axis about the balanced direction of the device suspended in a magnetic field.

BRIEF DESCRIPTION OF THE DRAWINGS

These and other objects and advantages of the present invention will become more apparent and more readily appreciated from the following description of the preferred embodiments, taken in conjunction with the accompanying drawings of which.

DETAILED DESCRIPTION OF THE PREFERRED EMBODIMENTS

Figure 1:
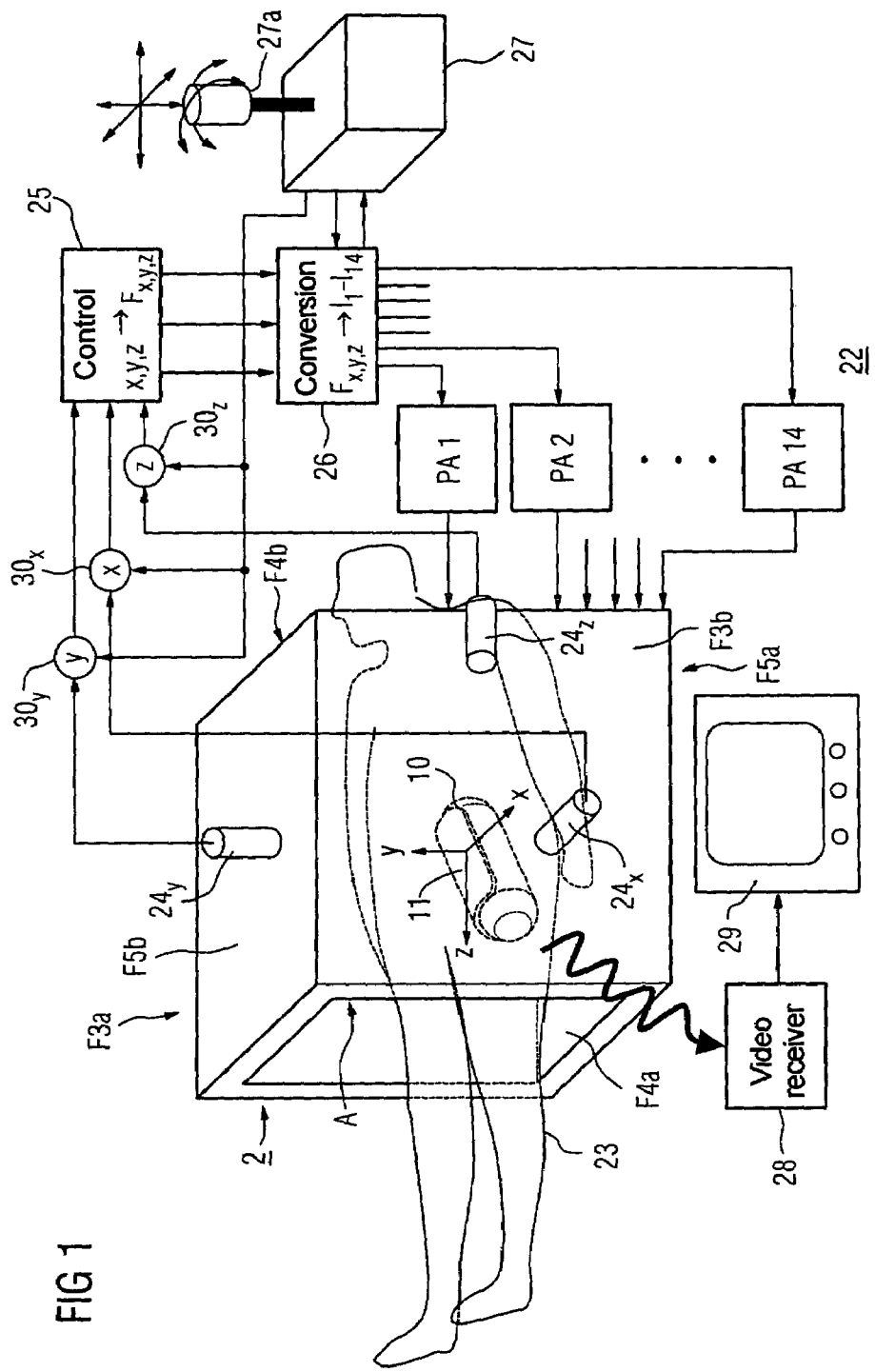
FIG. 1 is a block diagram of an installation for contactlessly moving and fixing/retaining a device according to the invention.
Figure 2:
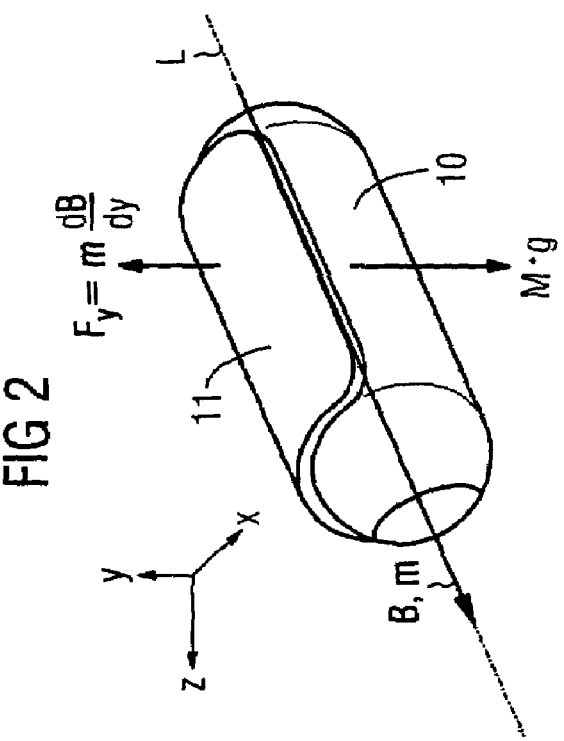
FIG. 2 is a perspective view of a first embodiment of a video camera oriented in a magnetic field.

Reference will now be made in detail to the preferred embodiments of the present invention, examples of which are illustrated in the accompanying drawings, wherein like reference numerals refer to like elements throughout.

A device based on the invention basically includes a nonmagnetic support structure for at least one magnet element which is rigidly connected thereto or is integrated therein. The shape of the support structure is inherently arbitrary and is generally dependent on the respective instance of application. By way of example, the support structure, as assumed for the exemplary embodiment in FIG. 1, has an elongate shape in the direction of a longitudinal axis. By contrast, the magnet element connected thereto needs to have a form which is stretched in one direction. The corresponding pronounced extent of the element may preferably point in the direction of the longitudinal axis of the support structure. The device can move contactlessly in a working volume and can stop there in stable fashion. In this case, the orientation and the size and direction of the forces on this device can be prescribed magnetically and without mechanical connection from the outside. Particularly in applications in medicine, a device including a magnet element and a support structure carrying the latter may thus be a catheter or an endoscope with a magnet element or a small television camera with lighting and a transmitter, which sends video images from inside the body, such as the digestive tract or the lung, and is moved by magnetic forces. Besides the application in the field of medical technology, particularly endoscopy, a device based on the invention may also be used just as well in other fields, such as in contaminated spaces. Thus, corresponding devices may also be used for inspecting other, in particular inaccessible, objects, for example internally, the devices naturally also being able to be equipped with other or additional functions.

Using a special magnet coil system, the device can be controlled by magnetic forces from outside in all three degrees of lateral freedom and in two degrees of rotary freedom in the viewing direction. The magnet coil system may be in a form such that access to its enclosed working volume is permitted in order, by way of example, to position people who are to be treated in the working volume. Details of an exemplary embodiment of a particularly suitable magnet coil system are the subject matter of DE application 103 40 925.4, which was not published prior to this, dated 09.05.2003 entitled "Magnetspulensystem zur beruhrungsfreien Bewegung eines magnetischen Elements in einem Arbeitsraum" [magnet coil system for contactless movement of a magnetic element in a working space].

FIG. 1 uses a block diagram to show an exemplary embodiment of an installation 22 for corresponding contactless navigation and fixing of a device 10 with a support structure and a magnet element 11 in a proband or object under examination 23, e.g. a person. In this instance, the proband is in a working space A, which is surrounded by fourteen individual coils in a magnet coil system 2 (not illustrated in more detail in FIG. 1). The device 10 may be, in particular, a probe such as a video capsule based on the aforementioned DE 101 42 253 C1 with an associated magnet element 11.

The magnet coil system 2 which is not illustrated in more detail in FIG. 1 has an approximately cuboid external contour, for example. The corresponding six cube faces are denoted F3a, F3b, F4a, F4b, F5a and F5b. The cube shall have an associated rectangular x, y, z co-ordinate system. In this case, the faces F4a and F4b situated at right angles to the z direction shall be regarded as end faces, while the pairs of faces F3a, F3b and F5a, F5b which are at right angles to the x axis and to the y axis can then be regarded as lateral pairs of faces. The pairs of faces enclose the three dimensional internal or working space A.

For active position control of the device 10 with the magnet element 11, the installation may use three detection units for detecting the actual position of the magnet element 11 and hence of the device 10 in the working space A. By way of example, these may be three position measuring elements $24_x$, $24_y$, and $24_z$ which are used to ascertain the position of the element 11 in the respective co-ordinate direction. The corresponding measured values are supplied to a control device 25 which is part of means for setting a nominal position for the magnet element. To this end, the control device includes three control loops for the x, y and z positions, which use the control error between the actual and nominal positions to produce opposing forces in the x, y and z directions on the magnet element 11. The control device 25 has a converter device 26 connected downstream of it. This converter device 26 controls fourteen power supply units PA1 to PA14 which are used to produce the currents $I_1$ to $I_{14}$ in the fourteen individual coils in the magnet coil system. In the coil system, a defined field direction and magnetic force F=degree (m·B) [m=vector of the magnetic moment of the element, B of the field] are produced on the magnet element 11. In this case, adjusting forces in the three co-ordinate directions, which forces are derived from the position control, are converted into magnetic fields and gradients and also into further coil currents which exert these forces on the magnet element. In this way, errors in the nominal position are counteracted and the position of the element is stabilized. As a consequence of this, free suspension involves the force due to weight and any other forces for overcoming mechanical resistances becoming established. An appliance 27 for setting the orientation, nominal position and direction of movement of the magnet element 11 or of the device 10, e.g. in the form of a joystick with a control stick 27a, or a 6D mouse, is used to prescribe the polar angles/co-ordinates θ and φ for the orientation and/or the nominal position and/or the direction of movement in the three spatial co-ordinates. To this end, the setting appliance 27 delivers the nominal positions x, y and z and compares them in respectively associated comparators $30_x$ and $30_y$ and $30_z$ with the actual position, which is obtained from the measured signals from the position measuring elements $24_x$, $24_y$ and $24_z$. The difference values are forwarded as control errors to the control device 25. There, they are amplified, processed further within the context of control engineering and supplied to the converter device 26. There, mathematical methods are used to calculate current values for the fourteen coil power supply units PA1 to PA14 from the values supplied in this manner, the current values being used to produce changed field gradients and hence magnetic forces $F_x$, $F_y$ and $F_z$ on the magnet element 11. These forces counteract the element's control error in its position x, y and z. In addition, the setting appliance 27 forwards to the converter device 26 the nominal directions using the polar angles θ and φ in the space, and the converter device converts these nominal directions into currents for the three field components $B_x$, $B_y$ and $B_z$ and forwards them to the coil system 2 as appropriate via the power supply units PA1 to PA14.

FIG. 1 also indicates an apparatus which is used to receive the video signal from a device 10 which is in the form of a video capsule and is equipped with a magnet element 11. To this end, the apparatus contains a video receiver 28 and a monitor 29.

Advantageously, the installation 2 may also be in a form such that the force on the magnet element 11 which is calculated in the converter device 26 exerts a proportional action of force on the joystick 27a of the setting appliance 27 via control elements in the appliance. This means that, by way of example, an unwanted mechanical resistance to the element 11 can be made perceptible to an operator of the setting appliance, for example an examining doctor.

In a further configuration of the installation, a position measurement through differentiation may advantageously be used to detect the speed of the device 10 with its magnet element 11 and to feed this speed into the control loop, with the aim of limiting it. This makes it possible to prevent, by way of example, damage as a result of the device's crashing into walls, e.g. inside the body of the proband 23.

Details of configuration options for a device 10 with a magnet element 11 can be found in FIGS. 2 to 5. In this case, it shall be assumed that the device is a cylindrical video capsule or video camera in line with DE 101 42 253 C1 with an end-face lens 12 whose outside has an elongate magnet element 11 mounted on it. The capsule is thus a support structure for the magnet element. This element is made either of highly retentive permanent magnetic material, such as NdBFe or SmCo, or of soft magnetic material with a high level of saturation magnetization, such as ingot iron, silicon iron or iron cobalt, which is magnetized as far as possible in the field of the surrounding coil system. In line with FIG. 2, the longitudinal axis L of the device is oriented in the direction of the local magnetic field of the induction B. Since, in line with the invention, the magnet element 11 is intended to be mounted asymmetrically with respect to the longitudinal axis L of the device 10, the device rotates in a working space fixed by an x, y, z co-ordinate system in interaction with the gravitational force M·g and the compensating magnetic force $F_y = m \cdot dB/dy$ in such a manner that the magnet element 11 comes to rest toward the top. In this case, B and m are the vectors of the magnetic field or of the magnetic moment and M is the total mass of the device 10 with the magnet element 11 and g is the acceleration due to gravity. In this way, the device 10 is permanently associated with "upwardly", i.e. counter to the gravitational force, pointing axes of the co-ordinate systems of the device and of the magnet system.

Figure 3A:
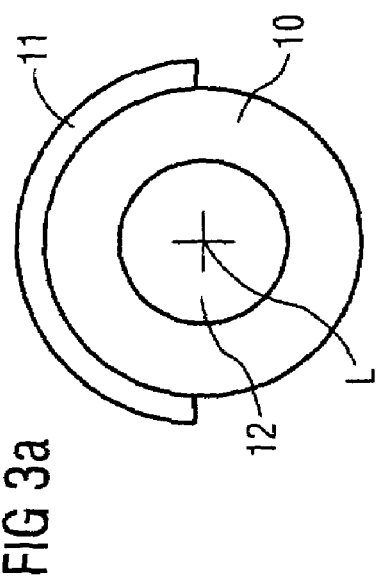
FIGS. 3a and 3b are a cross section and a longitudinal view, respectively, of the video camera illustrated in FIG. 2.
Figure 3B:
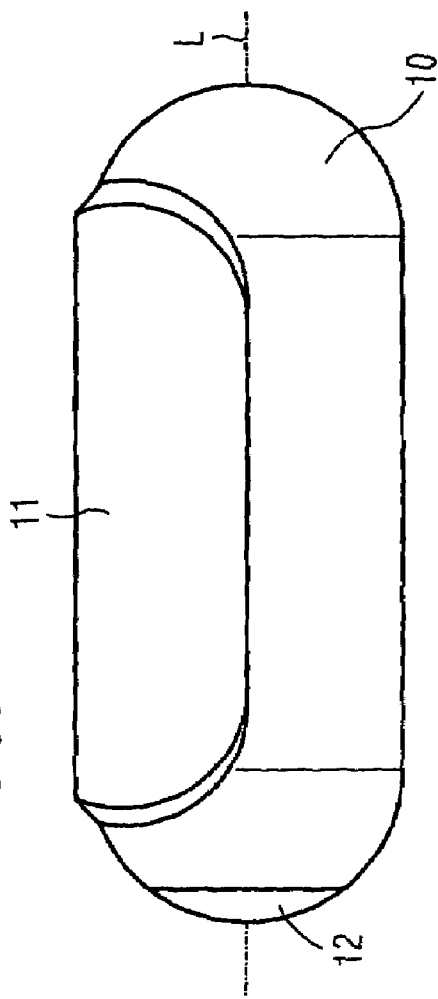

FIGS. 3a and 3b show a cross section and a side view of an elongate, cylindrical video camera or device 10 which serves as a support structure for a half-shell-like magnet element 11. The side view in FIG. 3b shows the saddle-like shape of this element in more detail.

The specific form of the magnet element 11 is not critical and is dependent on the respective instance of application. However, it needs to have a greater extent in one direction, particularly in the longitudinal direction L of the device 10, than in the other directions, in order to permit definite navigation in a magnetic field. Particularly in the case of biopsy applications, a sharp-edged design generally needs to be avoided, i.e. it is desirable to align or integrate the shape with or into the respective device.

Figure 4A:
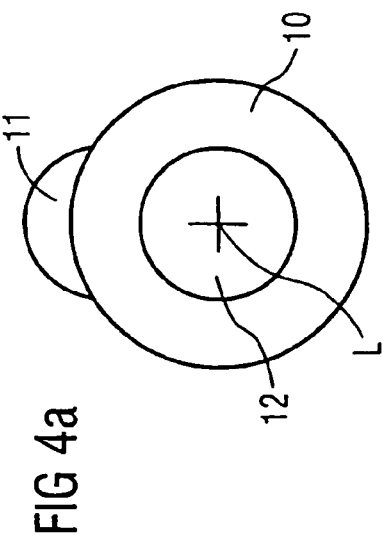
FIGS. 4a and 4b are a cross section and a longitudinal view, respectively, of a second embodiment of a video camera.
Figure 4B:
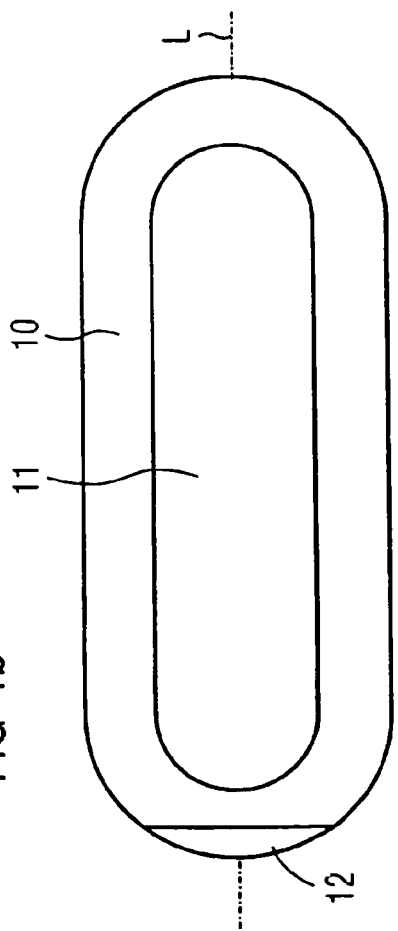

A design for a magnet element 11 in an approximate bar shape can be found in FIGS. 4a and 4b in an illustration based on FIGS. 3a, 3b.

Advantageously, in one specific embodiment of a magnet element 11, the latter's transverse dimension should not exceed half the length dimension, and the magnet mass should make up approximately 0.2 to 4 times the mass of the device 10 without the magnet element. This allows good navigability of the element in terms of the device 10 connected thereto to be insured.

Figure 5:
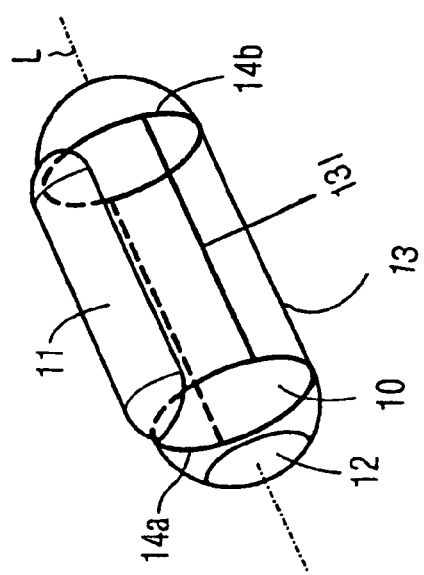
FIG. 5 is a perspective view of a device with shorted conductor loops.

As FIG. 5 reveals, there may additionally be shorted conductor loops 13i made of metals having good electrical conductivity, such as aluminum or copper, for eddy current damping and for damping angle oscillations by a magnet element 11 suspended in a magnetic field and hence also by the device 10. Thus, by way of example, a conductive cage 13 may be arranged on the outside of the device. This cage includes wire-like line parts 1 3i running parallel to the longitudinal axis L, it also being possible for the magnet element 11 to represent a further line part of the cage. These line parts are electrically connected to one another by end-face shorting rings 14a and 14b. However, individual loops with an angular offset from one another are also possible, these being able to extend along the longitudinal axis L of the device.

In line with a specific configuration of a device 10 based on the invention in line with FIGS. 3a, 3b, this device may have the following data:
weight of video capsule with batteries 4 g
magnetic field on the device 50 to 75 mT
magnet element 11 FeSi 0.2·1·2.5 $cm^3$, weight 4 g
field gradient upward (counter to the gravitational force)
    80 mT/m or as version with permanent magnets
NdBFe with $B_r$ is 1.2 T, 0.2·1.1·2.5 $cm^3$, weight 4 g
field gradient upward 130 mT/m.

In the exemplary embodiments above, it has been assumed that just one magnet element 11 extending in the longitudinal direction is provided. Such an element may naturally also include a plurality of sub-elements, or a plurality of discrete magnet elements may be used.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

What is claimed is:

1. A magnetically navigable device used in medical endoscopy, comprising:
    at least one magnetic element having a greater extent in a first direction than in a second direction at substantially 90 degrees to the first direction and having a central axis aligned in the first direction, where said at least one magnetic element is arranged asymmetrically with respect to the axis of said magnetically navigable device, said at least one magnetic element interacting with a gravitational force and a compensating magnetic force generated by magnetic field gradients which cause said at least one magnetic element to rotate around the axis of said magnetically navigable device to a to position which is counter to the gravitational force.

2. The magnetically navigable device as claimed in claim 1, further comprising a support structure with an exterior on which said at least one magnetic element is arranged.

3. The magnetically navigable device as claimed in claim 2, wherein the support structure has a shape at least substantially rotationally symmetrical with respect to a longitudinal axis of the magnetically navigable device.

4. The magnetically navigable device as claimed in claim 3, wherein the at least one magnetic element has a shape of one of a half-shell, a saddle, and a bar.

5. The magnetically navigable device as claimed in claim 4, wherein the at least one magnetic element has a transverse dimension no greater than half a longitudinal extent of said at least one magnetic element.

6. The magnetically navigable device as claimed in claim 5, wherein said at least one magnetic element has a mass between 0.2 times and 4 times that of said magnetically navigable device without said at least one magnetic element.

7. The magnetically navigable device as claimed in claim 6, further comprising means for eddy current damping using shorted conductor loops made of material having good electrical conductivity.

8. The magnetically navigable device as claimed in claim 7, wherein said magnetically navigable device is a video capsule.

9. The magnetically navigable device as claimed in claim 1, wherein said magnetically navigable device is an endoscopy video capsule.

10. The magnetically navigable device as claimed in claim 6, wherein said magnetically navigable device is a video capsule.

11. The magnetically navigable device as claimed in claim 5, wherein said magnetically navigable device is a video capsule.

12. The magnetically navigable device as claimed in claim 5, further comprising means for eddy current damping using shorted conductor loops made of material having good electrical conductivity.

13. The magnetically navigable device as claimed in claim 4, wherein said magnetically navigable device is a video capsule.

14. The magnetically navigable device as claimed in claim 4, further comprising means for eddy current damping using shorted conductor loops made of material having good electrical conductivity.

15. The magnetically navigable device as claimed in claim 4, wherein said at least one magnetic element has a mass between 0.2 times and 4 times that of said magnetically navigable device without said at least one magnetic element.

16. The magnetically navigable device as claimed in claim 3, wherein said magnetically navigable device is a video capsule.

17. The magnetically navigable device as claimed in claim 3, further comprising means for eddy current damping using shorted conductor loops made of material having good electrical conductivity.

18. The magnetically navigable device as claimed in claim 3, wherein said at least one magnetic element has a mass between 0.2 times and 4 times that of said magnetically navigable device without said at least one magnetic element.

19. The magnetically navigable device as claimed in claim 3, wherein the at least one magnetic element has a transverse dimension no greater than half a longitudinal extent of said at least one magnetic element.

20. The magnetically navigable device as claimed in claim 2, wherein said magnetically navigable device is a video capsule.

21. The magnetically navigable device as claimed in claim 2, further comprising means for eddy current damping using shorted conductor loops made of material having good electrical conductivity.

22. The magnetically navigable device as claimed in claim 2, wherein said at least one magnetic element has a mass between 0.2 times and 4 times that of said magnetically navigable device without said at least one magnetic element.

23. The magnetically navigable device as claimed in claim 2, wherein the at least one magnetic element has a transverse dimension no greater than half a longitudinal extent of said at least one magnetic element.

24. The magnetically navigable device as claimed in claim 2, wherein the at least one magnetic element has a shape of one of a half-shell, a saddle, and a bar.

25. The magnetically navigable device as claimed in claim 1, wherein said magnetically navigable device is a video capsule.

26. The magnetically navigable device as claimed in claim 1, further comprising means for eddy current damping using shorted conductor loops made of material having good electrical conductivity.

27. The magnetically navigable device as claimed in claim 1, wherein said at least one magnetic element has a mass between 0.2 times and 4 times that of said magnetically navigable device without said at least one magnetic element.

28. The magnetically navigable device as claimed in claim 1, wherein the at least one magnetic element has a transverse dimension no greater than half a longitudinal extent of said at least one magnetic element.

29. The magnetically navigable device as claimed in claim 1, wherein the at least one magnetic element has a shape of one of a half-shell, a saddle, and a bar.

* * * * *